(12) United States Patent
Wootten (10) Patent No.: US 8,218,133 B2
(45) Date of Patent: Jul. 10, 2012

(54) REFRACTIVE INDEX TOOL AND METHOD

(75) Inventor: Keith Robert Wootten, Hook (GB)

(73) Assignee: Sondex Limited, Yately, Hampshire (GB)

( * ) Notice: Subject to any disclaimer, the term of this patent is extended or adjusted under 35 U.S.C. 154(b) by 119 days.

(21) Appl. No.: 12/883,370

(22) Filed: Sep. 16, 2010

(65) Prior Publication Data

US 2012/0069328 A1    Mar. 22, 2012

(51) Int. Cl.
*G01N 21/41* (2006.01)
*G01B 9/02* (2006.01)

(52) U.S. Cl. ............... 356/133; 356/128; 356/481

(58) Field of Classification Search .......... 356/128–137; 343/783; 359/222.1, 586, 595, 598
See application file for complete search history.

(56) References Cited

U.S. PATENT DOCUMENTS

| | | | | |
|---|---|---|---|---|
| 3,448,616 A | * | 6/1969 | Heintz et al. ............ 73/293 |
| 4,608,344 A | * | 8/1986 | Carter et al. ............ 436/34 |
| 4,806,013 A | * | 2/1989 | Bodenheimer et al. ....... 356/133 |
| 5,311,274 A | * | 5/1994 | Cole, Jr. .............. 356/133 |
| 5,362,971 A | | 11/1994 | McMahon et al. |
| 5,600,433 A | * | 2/1997 | Buttry et al. ............. 356/128 |
| 5,712,934 A | * | 1/1998 | Johnson ............... 385/12 |
| 2004/0021849 A1 | * | 2/2004 | Kong et al. .............. 356/70 |

FOREIGN PATENT DOCUMENTS

| | | |
|---|---|---|
| CH | 512 060 | 8/1971 |
| EP | 0 508 894 A1 | 10/1992 |
| EP | 0 809 098 A1 | 11/1997 |
| EP | 1 617 202 A1 | 1/2006 |

OTHER PUBLICATIONS

Extended European Search Report and opinion issued in application No. EP 11181417, and mailed on Dec. 20, 2011.

* cited by examiner

*Primary Examiner* — Gregory J Toatley
*Assistant Examiner* — Jarreas C Underwood
(74) *Attorney, Agent, or Firm* — Potomac Patent Group PLLC (57) ABSTRACT

Refractive index tools and method. A refractive index tool includes a wave source configured to generate a wave; a transparent rod configured to receive the wave from the wave source; and a wave detector configured to receive the wave from the transparent rod. The wave source is provided at a first end of the transparent rod and the wave detector is provided at the first end or a second end of the transparent rod so that the wave emitted by the wave source travels through the transparent rod and experiences total internal refraction prior to arriving at the wave detector.

21 Claims, 7 Drawing Sheets

REFRACTIVE INDEX TOOL AND METHOD

BACKGROUND

1. Technical Field

Embodiments of the subject matter disclosed herein generally relate to methods and systems and, more particularly, to mechanisms and techniques for discriminating between various well fluids.

2. Discussion of the Background

Fossil fuel remains a major economic driver. Accordingly, the interest in developing new fossil fuel production fields continues to remain strong. In developing a new fossil fuel production field, a well may be drilled. A fossil fuel well may include different fluids including oil, water, and gas. It may be desirable to assess the mix of fluids in a well in developing a new production field.

In assessing the mix of fluids in a well, harsh environmental conditions may be encountered. For example, pressure in the well may rise to and even exceed fifteen-thousand to twenty-thousand (15,000-20,000) pounds per square inch and the temperature may rise to and even exceed one-hundred-eighty (180) degrees Celsius. Accordingly, current technologies for assessing the mix of fluids in a well are typically suitable for such harsh environmental conditions. Examples of current technologies for assessing the mix of fluids in a well may include capacitance and resistance array sensors. However, the range of methods for assessing the mix of fluids in a well is limited. Therefore, it may be desired to provide a novel approach for discriminating between various well fluids.

SUMMARY

According to an exemplary embodiment, there is a refractive index tool to discriminate between a plurality of fluids. The refractive index tool includes a wave source configured to generate a wave; a transparent rod configured to receive the wave from the wave source; and a wave detector configured to receive the wave from the transparent rod. The wave source is provided at a first end of the transparent rod and the wave detector is provided at the first end or a second end of the transparent rod so that the wave emitted by the wave source travels through the transparent rod and experiences total internal refraction prior to arriving at the wave detector. The refractive index tool is configured to measure an intensity of the wave received by the wave detector, the intensity of the wave being related to a refractive index of the transparent rod and a refractive index of a fluid in which the transparent rod is immersed, the refractive index of the transparent rod being higher than the refractive index of the fluid in which the transparent rod is immersed.

According to still another exemplary embodiment, there is a sensor device configured to be attached to a cable to be lowered into a well having a high temperature and/or a high pressure. The sensor device includes a first sensor; and a refractive index tool. The refractive index tool includes a wave source configured to generate a wave; a transparent rod configured to receive the wave from the wave source; and a wave detector configured to receive the wave from the transparent rod. The wave source is provided at a first end of the transparent rod and the wave detector is provided at the first end or a second end of the transparent rod so that the wave emitted by the wave source travels through the transparent rod and experiences total internal refraction prior to arriving at the wave detector. The refractive index tool is configured to measure an intensity of the wave received by the wave detector, the intensity of the wave being related to a refractive index of the transparent rod and a refractive index of a fluid in which the transparent rod is immersed, the refractive index of the transparent rod being higher than the refractive index of the fluid in which the transparent rod is immersed.

According to still another exemplary embodiment, there is an electronic circuit including a processor to execute a method for discriminating between a plurality of fluids. The method includes a step of generating a wave using a wave source, the wave to be received from the wave source into a transparent rod; a step of receiving the wave from the transparent rod into a wave detector; and a step of measuring an intensity of the wave received by the wave detector. The intensity of the wave is related to a refractive index of the transparent rod and a refractive index of a fluid in which the transparent rod is immersed, the refractive index of the transparent rod being higher than the refractive index of the fluid in which the transparent rod is immersed.

According to still another exemplary embodiment, there is a method for assembling a refractive index tool to discriminate between a plurality of fluids. The method includes attaching to a transparent rod a wave source configured to generate a wave; attaching to the transparent rod a wave detector configured to receive the wave from the wave source; connecting the wave source and the wave detector to an electronic circuit; and placing the wave source, the wave detector, and the electronic circuit within a housing. The refractive index tool is configured to measure an intensity of a wave received by the wave detector, the intensity of the wave being related to a refractive index of the transparent rod and a refractive index of a fluid in which the transparent rod is immersed, and the refractive index of the transparent rod being higher than the refractive index of the fluid in which the transparent rod is immersed.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of mechanisms and techniques for discriminating between various fluids in a fossil fluid well. However, the embodiments to be discussed next are not limited to such an application, but may be applied to other environments where discrimination between various fluids may be desirable.

Reference throughout the specification to "an exemplary embodiment" or "another exemplary embodiment" means that a particular feature, structure, or characteristic described in connection with an embodiment is included in at least one embodiment of the subject matter disclosed. Thus, the appearance of the phrases "in an exemplary embodiment" or "in another exemplary embodiment" in various places throughout the specification is not necessarily referring to the same embodiment. Further, the particular features, structures or characteristics may be combined in any suitable manner in one or more embodiments.

Figure 1:
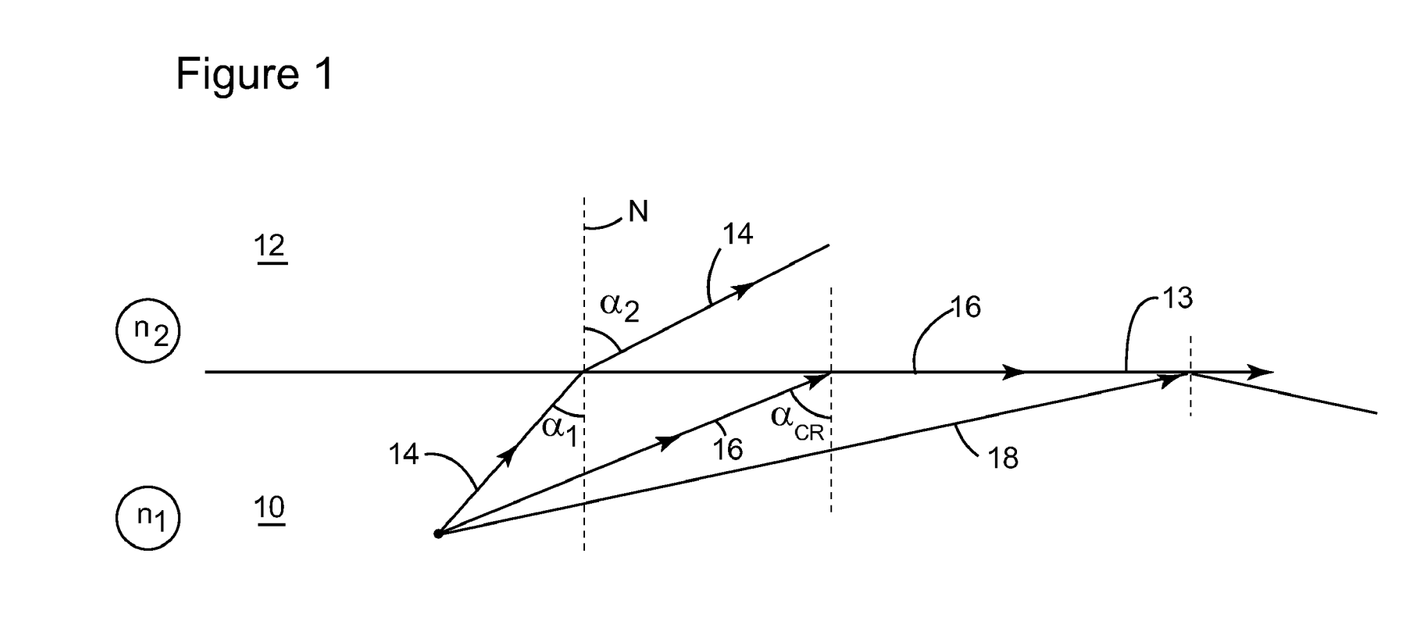
FIG. 1 is a schematic diagram illustrating a total internal refraction phenomenon.

Reference is made in the specification to refractive indices and total internal refraction. By way of background, a refractive index may be a number indicating the speed of light in a given medium. Light passing from one material (e.g., glass) into a second material having a lower reflective index (e.g., oil) may bend, depending on the incidence angle. That is, as illustrated in FIG. 1, a light ray 14 originating in, e.g., a medium 10 having an index of refraction n1 and traveling at an incident angle $\alpha 1$ relative to an axis N normal (e.g., substantially perpendicular to the interface 13 between medium 10 and medium 12) may bend (angle $\alpha 2$ is different from $\alpha 1$) when entering into, for example, a second medium 12 which may have a lower refractive index n2. It is known that the refraction angles $\alpha 1$ and $\alpha 2$ are related to each other by n1 $\sin(\alpha 1)$=n2 $\sin(\alpha 2)$. At a particular incident angle known as the critical angle $\alpha_{cr}$, the angle $\alpha 2$ of the light ray 16 becomes 90 degrees and the refracted ray may skim the surface of the first medium, remains inside the first medium. As illustrated in FIG. 1, such a light ray 16 originating in the first medium 10 and having an incident angle equal to the critical angle $\alpha_{cr}$ may have an angle of refraction that is 90 degrees and the refracted ray 16. For rays 18 traveling at an incident angle greater than the critical angle, all of the light may be reflected back into the first medium. As illustrated in FIG. 1, a light ray 18 originating in the first medium 10 and having an incident angle greater than the critical angle may be completely reflected in the first medium 10. This effect is referred to as total internal reflection (TIR). A condition for TIR is that the index of refraction of the second medium 12 is smaller than the index of refraction of the first medium 10, assuming that the source of light is placed in the first medium 10. Thus, part of the light 14 emitted from the source of light escapes the first medium 10 while part of the light 16 and 18 emitted by the source of light stays inside the first medium 10. These properties of the TIR are used in the following embodiments for discriminating among various mediums that may exist inside a well.

According to an exemplary embodiment, the refractive index of fluids in an oil well or similar environment may be measured by using a novel refractive index tool. The refractive index of the fluids in the oil well may be used to discriminate between various fluids in the well, including oil, water, and gas. The refractive index tool may be sufficiently small that multiple units may be used to obtain an image of the composition of the various fluids in the well, particularly non-vertical wells where, for example, any gas would naturally separate to form a topmost layer in the well. That is, it may be desirable to include a number of refractive index tools around the circumference of a cable or line that is lowered in the well because, for example, in a non-vertical well, gas, water, and oil phases may separate and occupy different parts of a bore of the well.

Figure 2:
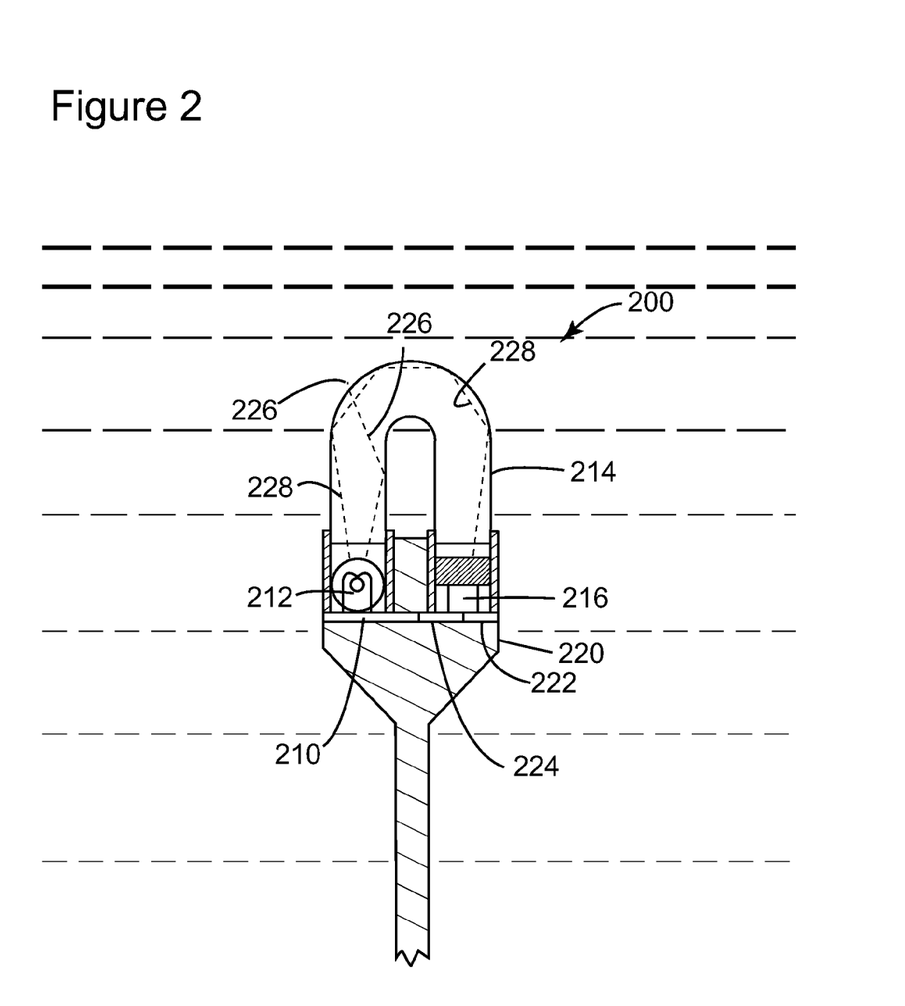
FIG. 2 is a schematic diagram of a refractive index tool according to an exemplary embodiment.

According to an exemplary embodiment shown in FIG. 2, a refractive index tool 200 may include a wave source 212 (such as a light source), a transparent rod 214 arranged to face the wave source 212 and to receive, at least a part of the waves emitted by the wave source 212. The term "transparent" is used here to indicate that the rod allows the propagation of the wave emitted by the wave source 212, i.e., the rod is transparent to that wave. Thus, the rod 214 should not be construed narrowly to only be transparent for a human eye. In one application the rod 214 may be transparent to the human eye but for other applications the rod 214 is not transparent to the human eye but for the wave emitted by the wave source 212. The wave source 212 may be a source of electromagnetic waves, including but not limited to visible light, infrared, etc. A wave detector 216 (such as a light detector) is provided at one end of the transparent rod 214 for receiving part of the waves emitted by the wave source 212 after traveling through the rod 214.

Figure 3:
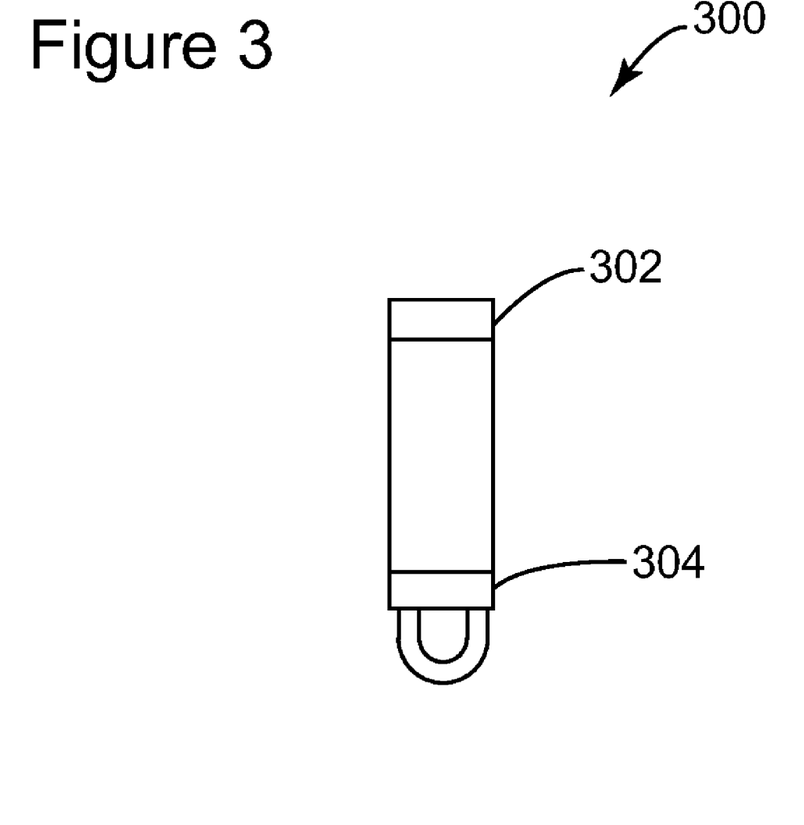
FIG. 3 is a schematic diagram of a device including a refractive index tool according to another exemplary embodiment.

An electronic circuit 218 is provided in electrical communication with one or more of the wave source 212 and the wave detector 216. All or part of these elements may be provided inside a housing 220. However, for exploiting the properties of the TIR, at least a portion of the rod 214 may be provided outside the housing so that this portion may directly contact a fluid inside the well. In one application, the refractive index tool 200 may be between two (2) and sixteen (16) centimeters in length. In another embodiment, the length of the refractive index tool may be lesser than or greater than between two (2) and sixteen (16) centimeters. In another exemplary embodiment shown in FIG. 3, a refractive index tool 304 may a part of a device 300 having other sensors 302. For example, as touched on above, the refractive index tool may be a part of a device having other refractive index tools so as to measure the refractive index of fluids at different points in an oil well or similar environment. As another example, the refractive index tool may be a part of a device having different sensors (e.g., flow sensors, dielectric sensors, etc.). Accordingly, the refractive index tool may act as another source of information backing up the information gathered by the different sensors thereby adding to the information that may be gathered during a test on a well.

Turning to FIG. 2, the wave source 212 may generate a wave (e.g., shine light) at a wide angle. Accordingly, with respect to light as an example, light rays may shine from the wave source in many different directions. The wave source may be a single frequency or wavelength wave source. In other exemplary embodiments, multiple wavelengths may be used to elicit more information from a well fluid either by using different frequency wave sources (with a broadband wave detector) or by using a broadband wave source (with a frequency discriminating wave detector).

The transparent rod 214 may be a U-shaped curved transparent rod, and may be formed of borosilicate glass. In another exemplary embodiment, the transparent rod may be formed of other materials such as glass or special plastics or other materials that transmit waves so long as the material can withstand the harsh environment of the well. The U-shaped curved transparent rod may be between one (1) and four (4) centimeters in length. The U-shaped curved transparent rod may have a radius of one (1) centimeter. In other exemplary embodiments (some of which are described below), the transparent rod 214 may have different shapes and sizes. The wave source 212 may be positioned at a first end of the U-shaped curved transparent rod such that a wave may be directed through the U-shaped curved transparent rod.

The wave detector 216 may be positioned at a second end of the U-shaped curved transparent rod as shown in FIG. 2. The wave detector 216 may be configured to provide an electrical output related to an intensity of a wave impinging on the wave detector 216. As noted above, in other exemplary embodiments, multiple wavelengths may be used to elicit more information from a well fluid by using a broadband wave detector (with different frequency wave sources) or a frequency discriminating detector (with a broadband wave source).

The electronic circuit 218 may be connected to the wave source 212 and the wave detector 216. The electronic circuit 218 may include a processor 222 and a storage device 224, e.g., a memory. The processor 222 of the electronic circuit 218 may control an emission of the wave source 212, a time of emitting light, may encode the electrical output from the wave detector 216 for acquisition and analysis and also may perform the analysis of the collected data. The encoded electrical output of the wave detector 216 may be stored in the storage 224, later retrieved from the storage 224 such as when the refractive index tool is retrieved from the well, and then analyzed and displayed on a screen. In another exemplary embodiment, the encoded electrical output may be transmitted via a wired or wireless connection from the refractive index tool 200 to a remote location for earlier (e.g., real-time) analysis and display on a computer screen.

The housing 220 may include the wave source 212, the wave detector 216, the electronic circuit 218 and a part of the rod 214. The U-shaped transparent rod 214 may be mounted such that both ends of the U-shaped transparent rod may be contained within the housing 220. The housing 220 may be sealed, and may prevent the fluid (e.g., oil or water) from reaching the wave source 212, the wave detector 216, the electronic circuit 218, and any other electronics. The housing 220 may be opaque. The housing 220 may include a battery to operate the wave source 212, the wave detector 216, and the electronic circuit 218. In another exemplary embodiment, the housing may receive a power wire from a remote source to provide power to the wave source, the wave detector, and the electronic circuit.

Figure 4:
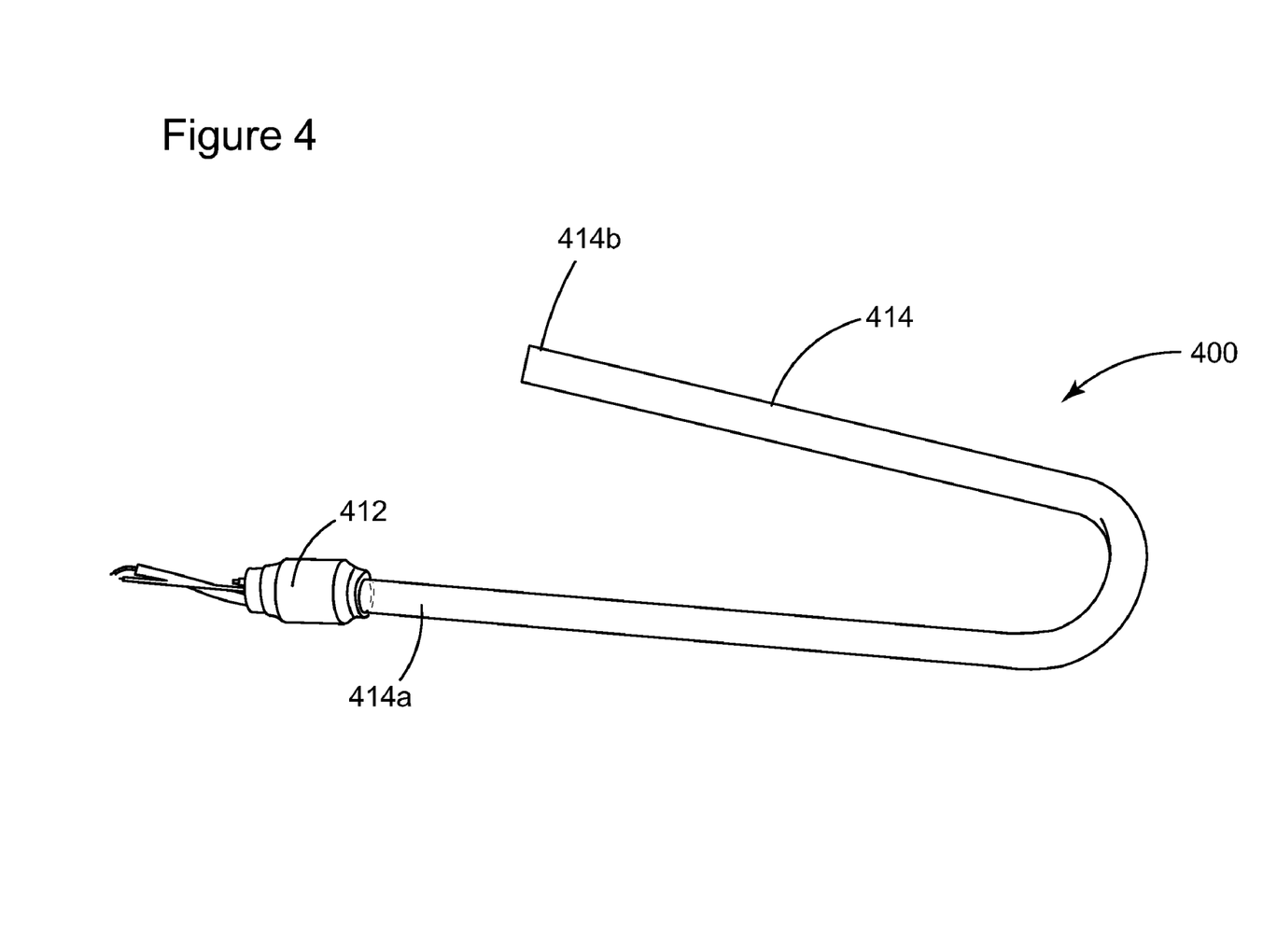
FIG. 4 is a schematic diagram of a refractive index tool according to another exemplary embodiment.

FIG. 4 is a schematic diagram of an actual refractive index tool 400 according to another exemplary embodiment wherein a wave detector, an electronic circuit, and a housing are not shown so as to aid in describing the operation of the refractive index tool 400. The operation of the refractive index tools 200 and 400 of FIGS. 2 and 4 are now described.

The refractive index tool 200 or 400 may be immersed in a fluid to be tested. This may be, for example, a fluid (liquid, gas, or combination thereof) existing in an oil well. As noted above, the refractive index tool may be a part of a device having other sensors, either additional refractive index tools, different sensors, or both. After an oil well drill line may be removed, the device including the refractive index tool may be lowered into the well and the refractive index tool may be deployed and then proceed to measure the refractive index of the fluid in the well as discussed below.

The light source 212 or 412 may generate a wave and may be connected to the transparent rod 214 or 414. The transparent rod may receive the wave from the wave source and may be connected to the wave detector 216. The wave detector may receive the wave from the transparent rod. The refractive index tool may measure an intensity of the wave received by the wave detector. The intensity of the wave is related to a refractive index of the transparent rod and a refractive index of a fluid in which the transparent rod is immersed. As the transparent rod is not coated to contain the wave inside it, part of the wave escapes the transparent rod and does not reach the wave detector. When the proper conditions for total internal refraction are met (e.g., appropriate shape of the transparent rod, correct relationship between the indexes of refraction for the medium and the rod), some of the wave (e.g., light) follows the shape of the transparent rod due to total internal refraction and arrives at the wave detector. Thus, the intensity of the wave arriving at the wave detector depends on the medium in which the rod is immersed. This process is described next in more details.

The wave source 212 or 412 may generate a wave (e.g., shine light) at a wide angle and much of the wave may exit the transparent rod 214 or 414 near the wave source. However, assuming the transparent rod has a higher refractive index than the fluid in the well, some of the waves may remain inside the rod 214 even when the rod is bent and thus, these waves may be received by the wave detector 216 due to the phenomenon of total internal reflection. Turning to FIG. 2, two exemplary wave rays 226 and 228 are shown. The first wave ray 226 is shown hitting the internal wall of the transparent rod 214 at an angle smaller than a critical angle of the transparent rod 214 and the fluid in which the transparent rod 214 is immersed. Accordingly, the first light ray 226 exits the transparent rod 214 to be absorbed in the fluid in which the transparent rod 214 is immersed. The second light ray 228 is shown hitting the internal wall of the transparent rod 214 at an angle larger than the critical angle of the transparent rod 214 and the fluid in which the transparent rod 214 is immersed. Accordingly, the second light ray 228 is reflected in a series of hops all the way to the wave detector 216.

The critical angle discussed with reference to the first and second rays 226 and 228 above depends on the ratio of the refractive indices of the transparent rod 214 and the fluid in which the transparent rod 214 is immersed. The refractive index of the transparent rod 214 may be fixed by the nature of the material of the transparent rod 214, and the refractive index of the fluid in which the transparent rod is immersed may vary between approximately 1 for a gas, 1.3 for water, and 1.5 for oil. The higher the refractive index of the fluid in which the transparent rod is immersed, the larger the critical angle and the less of the wave may be received by the wave detector 216. It should be noted that due to the harsh environment of a well, any, for example, oil may be burned off the transparent rod 114 when the transparent rod 114 is moved to, for example, gas. Thus, a possible problem of having the tool contaminated by oil when immersing it into gas is avoided.

Turning to FIG. 4, the immersion of the transparent rod 414 is now described with reference to three different fluids. First, the transparent rod 414 may be immersed in a gas (oxygen). The wave source 412 may generate a wave that may be received into the first end 414a of the transparent rod 414. The second end 414b of the transparent rod 414 is where the wave detector (not shown) may be positioned. The second end 414b of the transparent rod 414 may receive a wave of a high intensity. This is due to a small critical angle based on the refractive indices of the transparent rod and the gas (n=1).

Next, the transparent rod 414 may be immersed in water. The wave source 412 may generate a wave that may be received into the first end of the transparent rod 414. The second end of the transparent rod 414 may receive a wave of a lesser intensity than when the transparent rod is immersed in gas. This is due to a larger critical angle, the present critical angle being based on the refractive indices of the transparent rod and the water (n=1.3).

Next, the transparent rod 414 may be immersed in oil. The wave source 412 may generate a wave that may be received into the first end of the transparent rod 414. The second end of the transparent rod 414 may receive a wave of a lesser intensity than when the transparent rod is immersed in water. This is due to a larger critical angle, the present critical angle being based on the refractive indices of the transparent rod and the oil (n=1.5). Based on the above three examples, it is noted that the larger the critical angle, the smaller the intensity of wave arriving at the detector.

Figure 5:
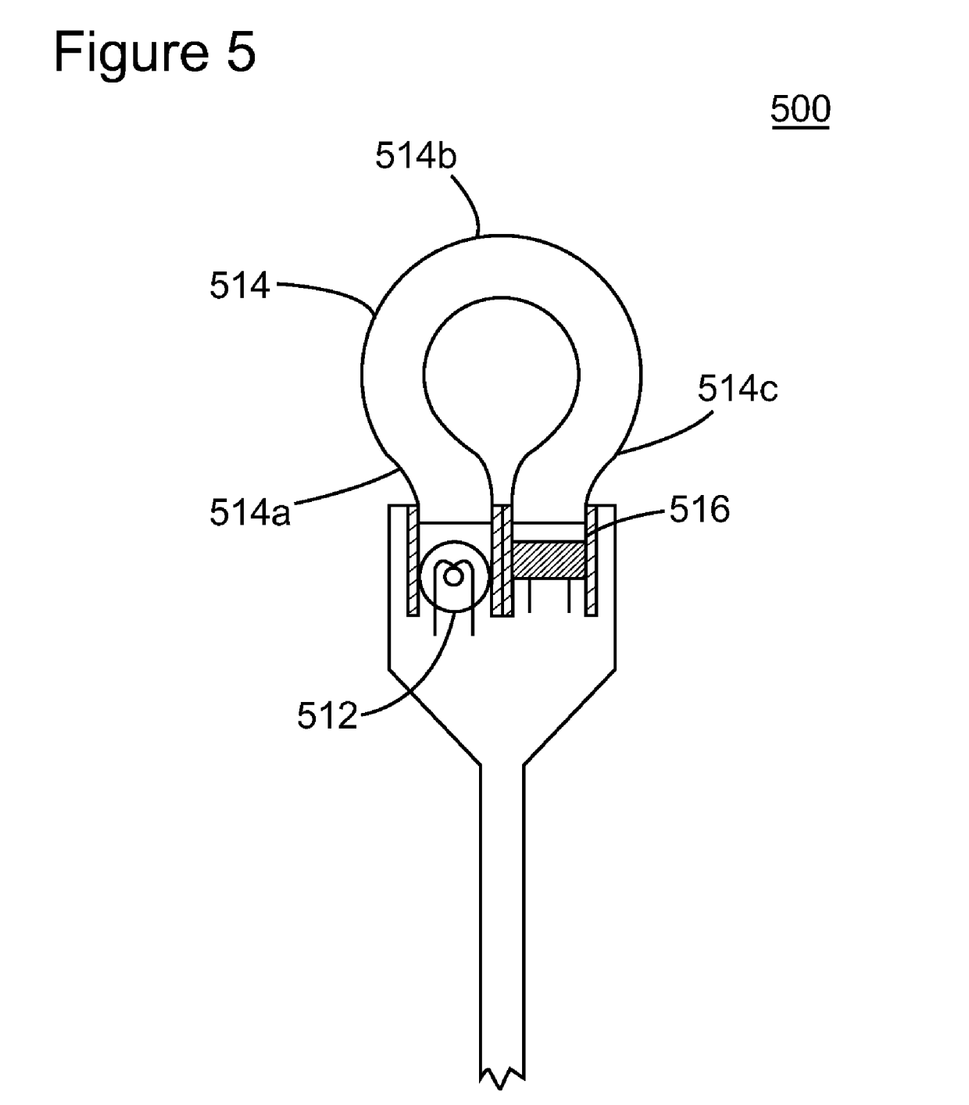
FIG. 5 is a schematic diagram of a refractive index tool according to another exemplary embodiment.

FIG. 5 is a schematic diagram of a refractive index tool 500 according to another exemplary embodiment. Various elements and operations of the refractive index tool 500 are similar to the elements and operations of the refractive index tools 200 and 400 of FIGS. 2 and 4. Consequently, the description of these similar elements and operations will not be repeated in the interest of brevity.

The refractive index tool 500 may include a wave source 512, a transparent rod 514, and a wave detector 516. The transparent rod 514 may be shaped such that a first end 514*a* may lead into a curved portion 514*b* and then into a second end 514*c* that is adjacent to the first end 514*a*. It should be noted that the transparent rod may be any appropriate shape, including a V-shape, a W-shape, or even an almost straight line. However, non-curved shapes may waste, for example, light. If the transparent rod has, for example, a V shape, the region of the V that forms the acute angle may be coated to prevent a wave from being lost at that region. The coating may selectively be used to cover parts of rods shaped different from the V shape. Turning to FIG. 5, the wave source 512 may be positioned at the first end 514*a* of the transparent rod 514 such that a wave may be directed into the transparent rod 514. The wave detector 516 may be positioned at the second end 514*c* of the transparent rod 514 to receive the wave from the transparent rod 514. The refractive index tool 500 may measure an intensity of the wave received by the wave detector 516. The intensity of the wave may be related to a refractive index of the transparent rod and a refractive index of a fluid in which the transparent rod 514 is immersed. Due to the curved shape of the transparent rod 514, the wave source 512 and the wave detector 516 may be positioned directly next to one another. Accordingly, the refractive index tool 700 may be compact in dimensions.

Figure 6:
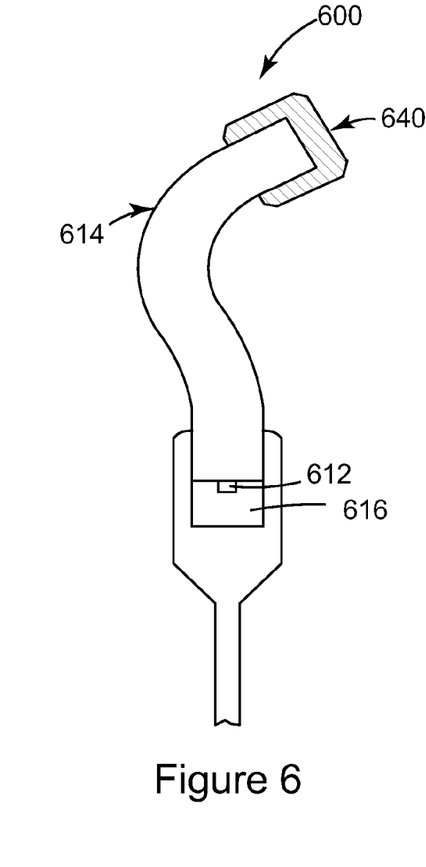
FIG. 6 is a schematic diagram of a refractive index tool according to another exemplary embodiment.

FIG. 6 is a schematic diagram of a refractive index tool 600 according to anther exemplary embodiment. Various elements and operations of the refractive index tool 600 are similar to the elements and operations of the refractive index tools 200 and 400 of FIGS. 2 and 4. Consequently, the description of these similar elements and operations will not be repeated in the interest of brevity.

The refractive index tool 600 may include a wave source 612, a transparent rod 614, and a wave detector 616. The transparent rod 614 may be curved. Accordingly, the wave source 612 and the wave detector 616 may be arranged so that there is little or no direct, for example, light path between the wave source 612 and the wave detector 616 except for the path through the transparent rod 614. The wave source 612 and the wave detector 616 may be housed in a same housing. The refractive index tool 600 may further include a reflective end piece 640 at a second end of the transparent rod 614. The reflective end piece may be silvered. The wave source 612 may be positioned at the first end of the transparent rod such that a wave may be directed into the transparent rod 614. The reflective end piece 640 may reflect back the wave into the transparent rod 614 (from the wave source 612). The wave detector 616 may also be positioned at the first end of the transparent rod to receive the wave from the transparent rod 614 (reflected by the reflective end piece 640). The refractive index tool 600 may measure an intensity of the wave received by the light detector 616. The intensity of the wave may be related to a refractive index of the transparent rod and a refractive index of a fluid in which the transparent rod 614 is immersed. Due to the lack of an almost full circle transparent rod, the refractive index tool 600 may be compact in dimensions. However, the transparent rod 614 may have at least one curved portion to make use of total internal refraction.

Figure 7:
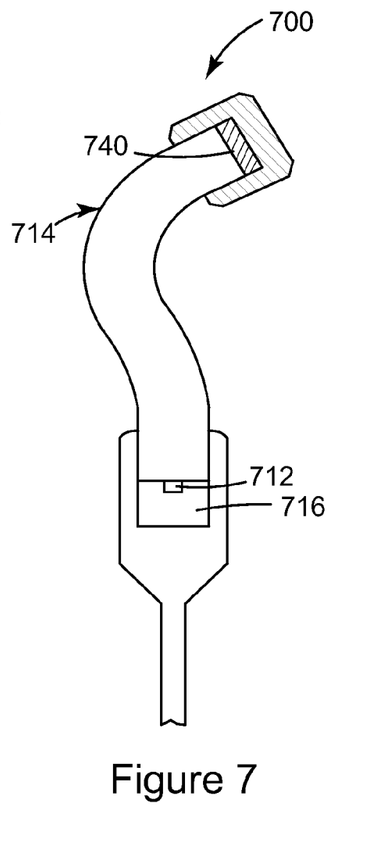
FIG. 7 is a schematic diagram of a refractive index tool according to another exemplary embodiment.

FIG. 7 is a schematic diagram of a refractive index tool 700 according to another exemplary embodiment. Various elements and operations of the refractive index tool 700 are similar to the elements and operations of the refractive index tools 200 and 400 of FIGS. 2 and 4. Consequently, the description of these similar elements and operations will not be repeated in the interest of brevity.

The refractive index tool 700 may include a wave source 712, a transparent rod 714, and a wave detector 716. The transparent rod 714 may be curved. Accordingly, the wave source 712 and the wave detector 716 may be arranged so that there is little or no direct, for example, light path between the wave source 712 and the wave detector 716 except for the transparent rod 714. The wave source 712 and the wave detector 716 may be housed in a same housing. The refractive index tool 700 may further include a phosphor coated end piece 740 at a second end of the transparent rod 714. The wave source 712 may be positioned at the first end of the transparent rod such that a non-visible wave such as ultraviolet light may be directed into the transparent rod 714. The phosphor coated end piece 740 may convert the non-visible wave from the transparent rod 714 (from the wave source 712) into a visible wave such as visible light and return this visible wave to the wave detector 716. The wave detector 716 may also be positioned at the first end of the transparent rod to receive the visible light (from the phosphor coated end piece 740). The wave detector 716 may not be sensitive to a non-visible wave such as ultraviolet light. Thus, even if waves from the wave source directly arrive at the wave detector 716, the readings of the wave detector 716 are not affected as the wave detector 716 is insensitive to the waves directly emitted by the source wave 712. The refractive index tool 700 may measure an intensity of a wave received by the wave detector 716. The intensity of the wave may be related to a refractive index of the transparent rod and a refractive index of a fluid in which the transparent rod 714 is immersed. Due to the lack of an almost full circle transparent rod, the refractive index tool 700 may be compact in dimensions. Due to the conversion of a non-visible wave into a visible wave, the optical isolation of the wave source 712 and the wave detector 716 may be easier to accomplish.

Figure 8:
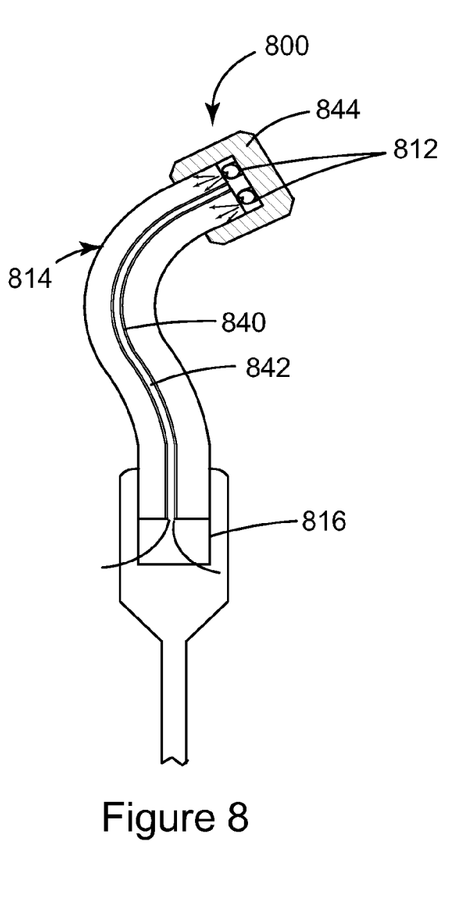
FIG. 8 is a schematic diagram of a refractive index tool according to another exemplary embodiment.

FIG. 8 is a schematic diagram of a refractive index tool 800 according to another exemplary embodiment. Various elements and operations of the refractive index tool 800 are similar to the elements and operations of the refractive index tools 200 and 400 of FIGS. 2 and 4. Consequently, the description of these similar elements and operations will not be repeated in the interest of brevity.

The refractive index tool 800 may include a wave source 812, a transparent rod 814, and a wave detector 816. The transparent rod 816 may be curved. The refractive index tool 800 may further include a capillary tube 840 positioned inside the transparent rod 814. The capillary tube 840 may be large enough to accommodate wires to be discussed next. The wave source 812 may be positioned at a second end of the transparent rod such that a wave may be directed into the transparent rod 814. The wave source 812 may be one or more LED lights. The wave source 812 may receive power via a power cable 842 placed through the capillary tube 840. The power cable 842 may be one or more fine power wires. The wave detector 816 may be positioned at the first end of the transparent rod to receive the wave from the transparent rod 814 (from the wave source 812). In another application, the positions of the wave source and wave detector may be reversed relative to the transparent rod. The refractive index tool 800 may measure an intensity of the wave received by the wave detector 816. The intensity of the wave may be related to a refractive index of the transparent rod and a refractive index of a fluid in which the transparent rod 814 is immersed. Due to the lack of an almost full circle transparent rod, the refractive index tool 800 may be compact in dimensions. For further increasing the efficiency of the wave source 812, a reflecting surface 844 may be provided around the wave source 812, so that all waves emitted by the wave source are directed towards the transparent rod 814.

Figure 9:
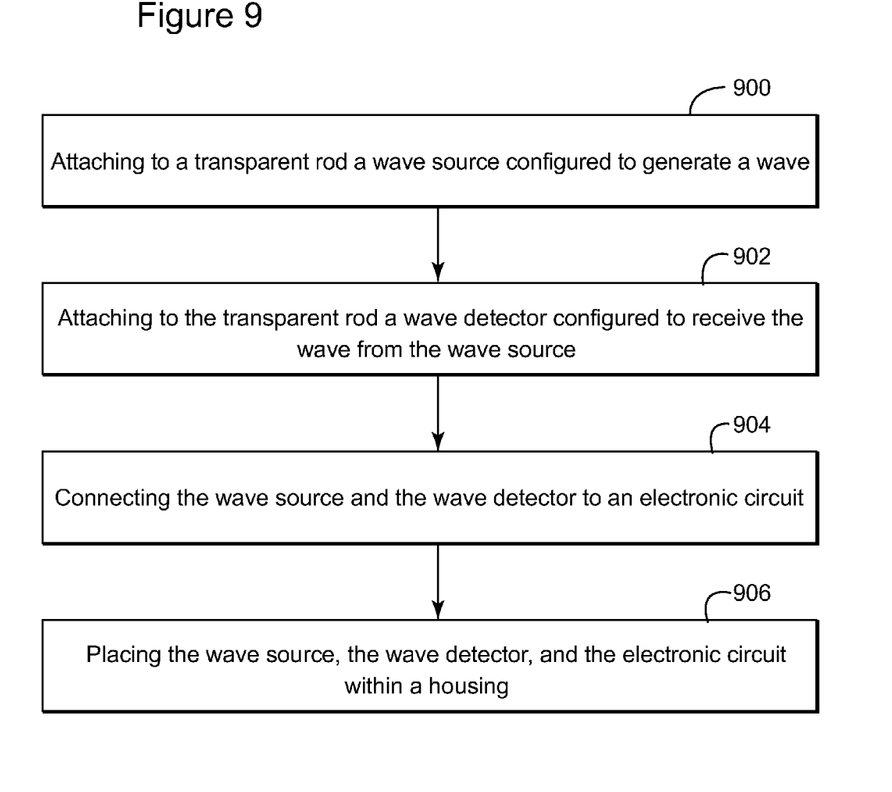
FIG. 9 is a flow chart of a method for manufacturing a refractive index tool according to an exemplary embodiment.

The assembly of a refractive index tool is now described with reference to FIGS. 2 and 9. A wave source 212 may be connected in step 900 to a first end of a transparent rod 214. A wave detector 216 may be connected in step 902 to the first end or a second end of a transparent rod 214. The wave source 212 and the wave detector 216 may be connected in step 904 to an electronic circuit 218. The wave source 212, the wave detector 216, and the electronic circuit 218 may be placed in step 906 within a housing 220.

Regarding a method of using the refractive index tool, it is noted that such a tool is provided inside a well by being immersed in a certain medium. A current is provided to the wave source to generate the wave and after the wave propagates through the transparent rod to the wave sensor, an intensity of the arriving wave is measured. This intensity depends on the index of refraction of the medium in which the transparent rod is immersed as the TIR dictates how much of the light is lost from the transparent rod and how much is maintained within the rod. Based on the measured intensity, a processor may look in a predetermined table to match the measured intensity with a corresponding index of refraction of the medium in which the transparent rod is immersed. The predetermined table may be populated prior to deploying the refractive index tool into the well. For example, various samples of gas, oil and water may be used in a control environment for collecting corresponding intensities with the refractive index tool and for generating the predetermined table or list. This data may be then stored either in a remote storage device or in the storage device 224 shown in FIG. 2 for further usage.

The disclosed exemplary embodiments provide refractive index tools and a method for discriminating between various well fluids. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A refractive index tool to discriminate between a plurality of fluids, the refractive index tool comprising:
   a wave source configured to generate a wave;
   a transparent rod configured to receive the wave from the wave source; and
   a wave detector configured to receive the wave from the transparent rod, wherein the transparent rod is a curved transparent rod,
   wherein the wave source and the wave detector are provided at a first end of the transparent rod so that the wave emitted by the wave source travels through the transparent rod and experiences total internal refraction prior to arriving at the wave detector, and
   wherein the refractive index tool is configured to measure an intensity of the wave received by the wave detector, the intensity of the wave being related to a refractive index of the transparent rod and a refractive index of a fluid in which the transparent rod is immersed, the refractive index of the transparent rod being higher than the refractive index of the fluid in which the transparent rod is immersed.

2. The refractive index tool of claim 1, wherein the transparent rod is a U-shaped curved transparent rod.

3. The refractive index tool of claim 1, further comprising:
   a reflective end piece positioned at the second end of the curved transparent rod to reflect the wave coming from the wave source back to the wave detector.

4. The refractive index tool of claim 1, further comprising:
   a phosphor coated end piece positioned at the second end of the curved transparent rod to reflect the wave coming from the wave source back to the wave detector,
   wherein the wave source is configured to generate a non-visible wave, the wave detector is not sensitive to the non-visible wave, and the phosphor coated end piece positioned at the second end of the curved transparent rod is configured to convert the non-visible wave into a visible wave to which the wave sensor is sensitive.

5. The refractive index tool of claim 1, wherein the curved transparent rod comprises:
   a capillary tube extending from the wave source to the wave detector,
   wherein the wave source is configured to receive power via a power cable through the capillary tube.

6. The refractive index tool of claim 1, further comprising:
   a housing including the wave source and the wave detector, wherein the housing is connected to the transparent rod.

7. The refractive index tool of claim 1, wherein the wave detector is configured to provide an electrical output related to the intensity of the wave impinging on the wave detector.

8. The refractive index tool of claim 7, further comprising:
   an electronic circuit connected to the wave source and the wave detector,
   wherein the electronic circuit is configured to control the wave source, to encode an electrical output from the wave detector, and to determine, based on a stored predetermined table, whether the fluid in which the transparent rod is immersed is air, water, or oil.

9. A sensor device configured to be attached to a cable to be lowered into a well having a high temperature and/or a high pressure, the sensor device comprising:
   a first sensor; and a refractive index tool, the refractive index tool including,
a wave source configured to generate a wave;
a transparent rod configured to receive the wave from the wave source, wherein the transparent rod is curved; and
a wave detector configured to receive the wave from the transparent rod,
wherein the wave source and the wave detector are provided at a first end of the transparent rod so that the wave emitted by the wave source travels through the transparent rod and experiences total internal refraction prior to arriving at the wave detector, and
wherein the refractive index tool is configured to measure an intensity of the wave received by the wave detector, the intensity of the wave being related to a refractive index of the transparent rod and a refractive index of a fluid in which the transparent rod is immersed, the refractive index of the transparent rod being higher than the refractive index of the fluid in which the transparent rod is immersed.

10. The sensor device of claim 9, wherein the first sensor is a refractive index tool.

11. The sensor device of claim 9, wherein the first sensor is a flow meter or a dielectric sensor.

12. The sensor device of claim 9, wherein the refractive index tool further comprises:
a housing including the wave source and the wave detector, wherein the housing is connected to the transparent rod.

13. The sensor device of claim 9, wherein the wave detector is configured to provide an electrical output related to the intensity of the wave impinging on the wave detector.

14. The sensor device of claim 13, wherein the refractive index tool further comprises:
an electronic circuit connected to the wave source and the wave detector,
wherein the electronic circuit is configured to control the wave source, encode an electrical output from the wave detector, and to determine, based on a stored predetermined table, whether the fluid in which the transparent rod is immersed is air, water, or oil.

15. A refractive index tool to discriminate between a plurality of fluids, the refractive index tool comprising:
a wave source configured to generate a wave;
a transparent rod configured to receive the wave from the wave source, wherein the transparent rod is curved; and
a wave detector configured to receive the wave from the transparent rod,
wherein the wave source is provided at a first end of the transparent rod and the wave detector is provided at a second end of the transparent rod so that the wave emitted by the wave source travels through the transparent rod and experiences total internal refraction prior to arriving at the wave detector,
wherein the transparent rod has a capillary tube extending from the wave source to the wave detector,
wherein the wave source is configured to receive power via a power cable through the capillary tube, and
wherein the refractive index tool is configured to measure an intensity of the wave received by the wave detector, the intensity of the wave being related to a refractive index of the transparent rod and a refractive index of a fluid in which the transparent rod is immersed, the refractive index of the transparent rod being higher than the refractive index of the fluid in which the transparent rod is immersed.

16. The refractive index tool of claim 15, further comprising:
a housing including the wave source and the wave detector, wherein the housing is connected to the transparent rod.

17. The refractive index tool of claim 15, wherein the wave detector is configured to provide an electrical output related to the intensity of the wave impinging on the wave detector.

18. The refractive index tool of claim 17, further comprising:
an electronic circuit connected to the wave source and the wave detector,
wherein the electronic circuit is configured to control the wave source, to encode an electrical output from the wave detector, and to determine, based on a stored predetermined table, whether the fluid in which the transparent rod is immersed is air, water, or oil.

19. A sensor device configured to be attached to a cable to be lowered into a well having a high temperature and/or a high pressure, the sensor device comprising:
a first sensor; and
a refractive index tool, the refractive index tool including,
a wave source configured to generate a wave;
a transparent rod configured to receive the wave from the wave source, wherein the transparent rod is curved; and
a wave detector configured to receive the wave from the transparent rod,
wherein the wave source is provided at a first end of the transparent rod and the wave detector is provided at a second end of the transparent rod so that the wave emitted by the wave source travels through the transparent rod and experiences total internal refraction prior to arriving at the wave detector,
wherein the transparent rod has a capillary tube extending from the wave source to the wave detector,
wherein the wave source is configured to receive power via a power cable through the capillary tube, and
wherein the refractive index tool is configured to measure an intensity of the wave received by the wave detector, the intensity of the wave being related to a refractive index of the transparent rod and a refractive index of a fluid in which the transparent rod is immersed, the refractive index of the transparent rod being higher than the refractive index of the fluid in which the transparent rod is immersed.

20. The sensor device of claim 19, wherein the first sensor is a refractive index tool.

21. The sensor device of claim 19, wherein the first sensor is a flow meter or a dielectric sensor.

* * * * *